United States Patent

Pedersen et al.

[11] Patent Number: 5,741,507
[45] Date of Patent: Apr. 21, 1998

[54] RANITIDINE TABLET HAVING A HYDROXYPROPYLMETHYLCELLULOSE CONTAINING COATING AND A METHOD FOR PRODUCING SAID COATING

[75] Inventors: Søren Bols Pedersen, Hvidovre; Knud Erik Gebhard-Hansen, Birkerød; Helle Kann, Frederiksberg, all of Denmark

[73] Assignee: A/S GEA Farmaceutisk Fabrik, Frederiksberg, Denmark

[21] Appl. No.: 732,383
[22] PCT Filed: Apr. 19, 1995
[86] PCT No.: PCT/DK95/00163
§ 371 Date: Jan. 15, 1997
§ 102(e) Date: Jan. 15, 1997
[87] PCT Pub. No.: WO95/28918
PCT Pub. Date: Nov. 2, 1995

[30] Foreign Application Priority Data

Apr. 22, 1994 [DK] Denmark ................ 0468/94

[51] Int. Cl.⁶ .................. A61K 47/00; A61K 9/68
[52] U.S. Cl. .................. 424/439; 424/440; 424/441; 424/465; 424/487; 424/489
[58] Field of Search .................. 424/439, 440, 424/441, 465, 487, 489; 514/974

[56] References Cited

U.S. PATENT DOCUMENTS

| 4,880,636 | 11/1989 | Franz ...................... 424/480 |
| 5,084,278 | 1/1992 | Mehta ...................... 424/441 |
| 5,635,200 | 6/1997 | Douglas et al. ........... 424/441 |

FOREIGN PATENT DOCUMENTS 2218336  11/1989  United Kingdom.

Primary Examiner—Joseph L. Schofer
Assistant Examiner—Kathryne E. Shelborne
Attorney, Agent, or Firm—Sughrue, Mion, Zinn, Macpeak & Seas, PLLC

[57] ABSTRACT

The present invention deals with a ranitidine tablet containing at least 30% ranitidine chloride and having a hydroxypropylmethylcellulose containing coating characterized in that the coating comprises hydroxypropylmethylcellulose and ethylcellulose in a mutual ratio between 10:1 and 1:2 as well as a method for producing the desired coating when manufacturing such ranitidine tablets.

6 Claims, No Drawings

RANITIDINE TABLET HAVING A HYDROXYPROPYLMETHYLCELLULOSE CONTAINING COATING AND A METHOD FOR PRODUCING SAID COATING

The present invention deals with a ranitidine tablet containing at least 30% ranitidine hydrochloride and having a hydroxypropylmethylcellulose containing coating as well as a method for producing the desired coating when manufacturing such ranitidine tablets.

It is conventional to provide a coating on pharmaceutical tablets for oral administration, either by dragging or by means of a film-coating technique, i.e. a process similar to a spray-painting.

The present invention is related to the use of this last mentioned technique on tablets containing ranitidine hydrochloride.

Usually coating of tablets for oral administration is performed for various purposes. Among such purposes are: improvement of the visual appearance of the tablets, that means colour, lustre etc., avoidance of unpleasant odour and taste by encapsulating active components having such unpleasant properties, reduction of friction to mucusae in throat and pharynx to make the tablets easier to swallow. Coating is also made with a purpose of protecting the active components of the tablets against moisture and light, thereby increasing the shelf-life of the tablets by delaying a decrease of activity and possibly discolouration caused by moisture and light.

However, it is important that the shielding of the tablets against the surroundings performed by the tablet coating is not so efficient that the bioavailability of the administered drugs be decreased to any substantial extent due to prevention or delaying of the disintegration of the tablet in the intestine or due to prevention of delaying of dissolution of the active substance from the tablet out into the digesting liquids.

Ranitidine, having the IUPAC-name N-[2-[[[5-(dimethylamino)-methyl-2-furanyl]methyl]thio]ethyl]-N'-methyl-2-nitro-1,1-ethendiamine, is a $H_2$-receptorantagonist which is extensively used for treating gastric ulcer. It is used as the hydrochloride salt and is mainly administered as tablets for oral use.

The activity of ranitidine is at such a level that ranitidine tablets are suitably marketed having a contents of ranitidine hydrochloride from approximately 100 mg to a few hundred mgs. This means that it is desired that the amount of excipients and adjuvants in the tablets is kept relatively low to avoid that the tablets become too large and thereby unpleasant to swallow. For this reason it is preferred that the ranitidine hydrochloride constitutes at least 30% of the tablet.

Since ranitidine hydrochloride is hygroscopic and is degraded by moisture and light whereby a decrease in activity and especially a discolouration takes place, there is a special need for an effective coating of ranitidine hydrochloride tablets.

However, ranitidine hydrochloride has properties rendering it difficult to provide the tablets with a coating which is effectively protecting, but which does not decrease the bioavailability.

This is probably due to the fact that ranitidine hydrochloride due to the very high solubility thereof in water and in many organic liquids penetrates up through the applied coating during the drying thereof and also subsequently under the influence of humidity in the air. The amount of ranitidine hydrochloride, which penetrates through the coating or just migrates up into the coating, will be subjected to a rapid discolouration under influence of light and moisture.

An obvious possibility for reducing said problems connected to coating of ranitidine hydrochloride tablets would be to reduce the unfortunate action of the ranitidine hydrochloride by applying a larger amount of inert excipients in the tablet composition. However, due to the above mentioned desire of keeping the amount of ranitidine hydrochloride at at least 30%, this possibility is not commercially acceptable.

Thus, coating of ranitidine tablets involves special problems. It has been suggested (cf. published Danish patent application No. 2337/89) to solve some of the problems related to coating of ranitidine hydrochloride tablets by using a coating of hydroxypolymethylcellulose containing as plastifier triacetine. Triacetine is a plastifier which previously had found general applicability in tablet coatings, also together with hydroxypropylmethylcellulose.

The coatings on ranitidine hydrochloride tablets disclosed in said patent application have, however, certain drawbacks and this, to a certain extent, also applies to the coating processes dealt with in the application.

This is primarily due to the fact that hydroxypropylmethycellulose without a substantial contents of other film-forming polymers produces a film-coating being rather permeable for water vapour and for ranitidine hydrochloride. The latter can migrate out into the coating and even reach the surface thereof where it will be degraded and discoloured unless the coating is sufficiently thick to balance this permeability.

Therefore, the coatings used on the tablets according to said patent application are relatively thick, corresponding to an amount of polymer coating forming 2.1–5.0, preferably 3.0–4.0, parts by weight per 100 parts by weight of the tablets.

It is stated that this prior art coating can be applied both as an aqueous solution and as a solely organic solution followed by evaporation of the solvent.

However, due to the present requirements as to protection of the environment the use of purely organic solvents, especially chlorinated hydrocarbons, as suggested in the application, will hardly come into consideration.

When applying coatings using solutions having a substantial water content, it is problematic to apply especially thick layers at least when cellulose derivatives are involved.

This is due to the fact that the technique used by atomizing the solutions in question involves certain limitations as to the maximum viscosity of the solutions. This means that the dry solids contents in the solutions are restricted for which reason evaporation of a substantial amount of water is required when a relatively thick coating shall be applied.

Inter alia due to the well-known relatively large heat of evaporation for water a relatively prolonged treatment of the tablets at lenient drying conditions will be necessary. Consequently the coating process becomes slow and the capacity for a given apparatus will be low. Besides it has turned out that such relatively thick coatings produced by drying of aqueous solutions often do not adhere sufficiently to the surface of the ranitidine hydrochloride tablets, especially if the coating process has not been performed sufficiently slowly.

The problem caused by the migration of the ranitidine hydrochloride through the coating film could in principle be dissolved by coating the tablet core first with a thin layer of ethylcellulose in a solvent based on chlorinated hydrocarbons in a first step, and thereafter, after evaporation of the solvent, to apply an aqueous hydroxypropylmethylcellulose solution in a second step, which last mentioned solution could further comprise the necessary pigments, plastifiers and other usual adjuvants.

For environmental reasons the first step of such a process requiring use of chlorinated hydrocarbons is, however, undesired and besides other problems arise due to the high solubility of the ranitidine hydrochloride in water. Due to this high solubility a ranitidine hydrochloride tablet after ingestion will normally be dissolved from the surface and will not blow up since the concentrated solution of ranitidine hydrochloride at the tablet surface will delay further migration of water into the core, for which reason the usual blowing agents in the tablets will not contact the amount of water necessary for causing blowing of the tablets.

This means that the ethylcellulose film on one hand should be so dense that it prevents introduction of water to the core during application of the hydroxypropylmethylcellulose film from an aqueous solution, but on the other hand it should not be so dense that it prevents water to penetrate the film in a short time, this means 15–30 seconds, to a sufficient extent to loosen the coating from the tablet core. If the film becomes substantially more dense, the result could easily be a tablet having delayed release of the active substance, and this is not desired since thereby large variations of the bioavailability of the tablet can result.

Therefore, such a two-step coating has not only the drawbacks that it uses chlorinated hydrocarbons undesired for environmental reasons and is demanding, it is also difficult to operate and control.

It has now turned out that by using a coating material which as sole or essential film-forming polymer component has a combination of hydroxypropylmethylcellulose (as defined below) and ethylcellulose (as defined below) the above specified requirements for tablet coatings on ranitidine hydrochloride tablets can be fulfilled using a coating thickness less than what is usual for the coatings according to Danish patent application No. 2337/89, and at the same time the coating process can be performed without problems.

The invention is not restricted to any special theory why the surprising results are obtained, but it is assumed that the ethylcellulose makes the coating less penetratable to water vapour and imparts a better resistance against migration of ranitidine hydrochloride through the layer than what applies to a layer of hydroxypropylmethylcellulose alone. However, at the same time the fact that the coating is thinner than the prior art hydroxypropylmethylcellulose coatings implies that the bioavailability is not impaired in relation to what applies for the prior coatings.

Consequently the ranitidine tablet according to the invention is characterized in that the coating comprises hydroxypropylmethylcellulose and ethylcellulose in a mutual weight ratio of from 10:1 to 1:2. Preferably this weight ratio is from 4:1 to 1:1, typically 2:1.

The hydroxypropylmethylcellulose which comes into consideration is a such, which as an aqueous 2% by weight solution at 20° C. has a viscosity between 2 and 18 mPas, preferably between 4.0 and 7.2 mPas. The preparation especially prefered is hydroxypropylmethylcellulose 2910 which is defined as a propyleneglycolether of methylcellulose containing at least 7.0% and at most 12.08 hydroxypropoxy and at least 28.0% and at most 30.0% methoxy, calculated on dry basis.

The ethylcellulose coming into consideration is an ethylether of cellulose which after drying at 100° C. for 2 hours contains at least 44.0% and at most 51.0% ethoxy groups.

Apart from said cellulose derivatives the coating can contain various adjuvants which are usual in such coatings such as conventional plastifiers, e.g. propyleneglycol, triacetine, triethylcitrate etc., colourants and pigment preparations containing especially titandioxide of ironoxide. Moreover, a vegetal oil and/or further adjuvants such as polyvinylpyrrolidone can be used for plastifying or as antifriction agents.

The thickness of the coating is suitably such that it corresponds to from 1 to 2.5% by weight hydroxypropylmethylcellulose+ethylcellulose, calculated on the tablet weight, preferably from 1.5 to 2.0% by weight, typically 1.7% by weight. Coatings having this thickness have proven to be optimal since they by a simple and quick coating procedure apply the desired properties to the tablets, especially as to protection against discolouration at shelving, without creating undesired properties as to bioavailability of the ranitidine.

Because hydroxypropylmethylcellulose and ethylcellulose, as defined above, have quite different characteristics as to solubility, one would have expected it to be impossible to apply the two substances dissolved in a common solvent in a sufficient concentration for securing the necessary amount of pigment substances necessary to protect the ranitidine hydrochloride against light.

However, it has turned out that by using a solvent medium consisting of an aqueous alcohol where the alcohol is selected among methanol, ethanol., normal propanol and isopropanol, and preferably is ethanol, having a carefully selected ratio of alcohol to water, the hydroxypropylmethylcellulose and ethylcellulose can be dissolved in the desired ratio and in the desired concentration to enable production of the above described coating in a single step using conventional coating technique.

Accordingly, the invention also deals with a process for producing the ranitidine tablets according to the invention, which process is characterized in that a solution is manufactured containing from 2.5 to 9% by weight hydroxypropylmethylcellulose and from 1.5 to 6% by weight ethylcellulose and which, in dissolved an/or suspended state if desired, also contains usual plastifiers, colourants and pigments and other conventional adjuvants, in an aqueous alcohol having a content of 72.5–82.5% by weight of an alcohol selected among methanol, ethanol, n- and isopropanol, and the solution is by spraying applied onto ranitidine hydrochloride containing tablets which are kept moving in a stream of drying air at such a temperature that the aqueous alcohol evaporates.

Preferably the solution is prepared having a content of 7–15% by weight hydroxypropylmethylcellulose plus ethylcellulose in an aqueous approximately 78% by weight ethylalcohol.

The process can be performed using any of the apparatuses conventional for similar purposes. Especially satisfactory results have been obtained using apparatuses in which the tablets in fluidized condition perform a swirling movement while being coated with the solution which is atomized throught a two-fluid nozzle.

The coating which is produced by the process of the present invention will usually adhere sufficiently to the surface of the ranitidine hydrochloride tablets, probably because the relatively small thickness does not give rise to inclusion of liquid or gas between the tablet surface and the coating. However, to ensure a sufficient adhesion also at varying operational conditions it is preferred to add a surfactant to the solution which is going to be sprayed onto the tablets. As such surfactant it is preferred to use Polysorbate 80.

The invention is further illustrated by means of the following embodiment example.

EXAMPLE 534 g ethylcellulose (10 centipoise) were dissolved in 13289 g 99.9% by weight ethanol, and 120 g polyvinylpyrrolidone were dissolved in the resulting solution. 1066 g hydroxypropylmethylcellulose and 533 g titandioxide and subsequently the following components were added and admixed in the order listed: 100 g Macrogol 400 (a polyethyleneglycol, plasticizer), 200 g propyleneglycol (plasticizer), 100 g Polysorbate 80 (surfactant) and 200 g soybean oil (plasticizer and anti-friction agent).

Subsequently 3858 g purified water were added to the stirred mixture to obtain a total charge weigheing 20 kg.

The mixture was agitated during 5 hours by means of a mechanical stirring system to ensure complete dissolving of the hydroxypropylmethylcellulose.

Convex, non-coated raniditine hydrochloride tablet cores each containing ranitidine corresponding to 150 mg free base were manufactured in conventional way by adding pharmaceutically acceptable adjuvants of the groups binding agents, blowing agents and glazing agents to obtain a core weight of 230 mg/core.

800 g of these cores were introduced into a coating apparatus having a capacity of 1 kg, and the coating solution was applied by means of a two-fluid nozzle. For each core 8 mg dry solids were applied corresponding to 1.9 parts by weight hydroxypropylmethylcellulose+ethylcellulose per 100 parts by weight tablet cores.

The tablet cores were provided with embossed numbers and letters. These were not blurred by the coating but appeared just as sharp and easily legible as on the non-coated cores.

The coated tablets were without any discolouration, and even after having been kept for extended periods under normal conditions the tablets maintained their appearance.

We claim:

1. Ranitidine tablet having a contents of at least 30% ranitidine hydrochloride and having a coating containing hydroxypropylmethylcellulose, characterized in that the coating comprises hydroxyproplylmethylcellulose and ethylcellulose in a mutual ratio between 10:1 and 1:2.

2. Ranitidine tablet according to claim 1, characterized in that the weight ratio of hydroxypropylmethylcellulose to ethylcellulose is from 4:1 to 1:1.

3. A process for producing the desired coating when manufacturing ranitidine tablets as defined in claim 1, characterized in preparing a solution containing from 2.5 to 9% by weight hydroxypropylmethylcellulose and from 1.5 to 6% by weight ethylcellulose and, optionally, in dissolved and/or suspended form, usual plasticizers, colourants and pigments and other conventional adjuvants, in an aqueous alcohol comprising 72.5–82.5% by weight of an alcohol selected among methanol, ethanol, n- and isopropanol, and by spraying applying the solution on ranitidine hydrochloride containing tablets while these are kept moving in a stream of drying air having such a temperature that the aqueous alcohol evaporates.

4. A process according to claim 3, characterized in that the solution is prepared having a contents of hydroxypropylmethylcellulose plus ethylcellulose amounting to 7–15% by weight in an aqueous approximately 78% by weight ethylalcohol.

5. A process according to claim 3, characterized in that also a surfactant is incorporated into the solution.

6. A process according to claim 5, characterized in that the surfactant is Polysorbate 80.

* * * * *